US011596531B2

(12) United States Patent
Pawlik et al.

(10) Patent No.: US 11,596,531 B2
(45) Date of Patent: Mar. 7, 2023

(54) PROSTHETIC SOCKET SYSTEM, AND PROSTHETIC SOCKET AND LINER (71) Applicant: OTTO BOCK HEALTHCARE PRODUCTS GMBH, Vienna (AT)

(72) Inventors: Roland Pawlik, Vienna (AT); Johan Nieuwendijk, Vienna (AT); Dries Glorieux, Lommel (BE); Luder Mosler, Duderstadt (DE)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 0 days.

(21) Appl. No.: 16/097,181

(22) PCT Filed: Apr. 28, 2017

(86) PCT No.: PCT/EP2017/060174
§ 371 (c)(1),
(2) Date: Oct. 26, 2018

(87) PCT Pub. No.: WO2017/186902
PCT Pub. Date: Nov. 2, 2017

(65) Prior Publication Data
US 2019/0091043 A1 Mar. 28, 2019

(30) Foreign Application Priority Data
Apr. 29, 2016 (DE) .......................... 102016108046.2

(51) Int. Cl.
A61F 2/78 (2006.01)
A61F 2/80 (2006.01)
A61F 2/50 (2006.01)

(52) U.S. Cl.
CPC .............. *A61F 2/7812* (2013.01); *A61F 2/80* (2013.01); *A61F 2002/5026* (2013.01); *A61F 2002/7875* (2013.01); *A61F 2002/7881* (2013.01)

(58) Field of Classification Search
CPC .. A61F 2/7812; A61F 2/80; A61F 2002/5026; A61F 2002/7875; A61F 2002/7881
(Continued)

(56) References Cited

U.S. PATENT DOCUMENTS 7,488,349 B2   2/2009   Einarsson
8,999,004 B2   4/2015   Abu Osman et al.
(Continued)

FOREIGN PATENT DOCUMENTS

CN   101410073 A   4/2009
CN   201727613 U   2/2011
(Continued)

OTHER PUBLICATIONS

PCT International Search Report for PCT International Patent Application No. PCT/EP2017/060174, dated Jul. 27, 2017.

*Primary Examiner* — Jerrah Edwards
*Assistant Examiner* — Aren Patel
(74) *Attorney, Agent, or Firm* — Holland & Hart LLP (57) ABSTRACT A prosthetic socket system comprising a prosthetic socket and a liner, said prosthetic socket having a distal end region, at least one socket wall extending therefrom in proximal direction, and connection means for securing a prosthetic component. The socket wall, when in the applied state, at least partially enclose a stump that is received in the prosthetic socket The liner includes a proximal entry opening and a lateral wall which extends in the distal direction, at least partially surrounds a stump when in the applied state and is arranged between the stump and the prosthetic socket (Continued)

when in the applied state. A coupling device is arranged between the liner and the prosthetic socket in the distal end region, and, on the outer side of the lateral wall of the liner and on the inner side of the socket wall, resistance regions are arranged or formed which interact with one another and which counteract a movement extracting said liner out of the prosthetic socket, in the proximal direction.

29 Claims, 8 Drawing Sheets

(58) Field of Classification Search
USPC .......................................................... 623/36
See application file for complete search history.

(56) References Cited

U.S. PATENT DOCUMENTS

| 9,241,813 B2 | 1/2016 | Hillmann |
| 2009/0036999 A1* | 2/2009 | Egilsson ............... A61F 2/7812 623/36 |
| 2009/0187140 A1 | 7/2009 | Racz |
| 2010/0004756 A1 | 1/2010 | Horie |
| 2013/0053982 A1* | 2/2013 | Halldorsson .......... A61F 2/7812 623/36 |
| 2013/0123940 A1 | 5/2013 | Hurley et al. |
| 2014/0005469 A1 | 1/2014 | Yao et al. |
| 2014/0121783 A1* | 5/2014 | Alley .................... A61F 5/0102 623/33 |
| 2014/0277584 A1 | 9/2014 | Hurley et al. |
| 2015/0051693 A1 | 2/2015 | Bertolino et al. |
| 2015/0105867 A1 | 4/2015 | Novak |
| 2016/0278949 A1* | 9/2016 | Dillingham ............... A61F 2/54 |
| 2017/0056212 A1* | 3/2017 | Jonsson .................... A61F 7/00 |
| 2017/0105853 A1* | 4/2017 | Jonsson ................ A61F 2/7812 |
| 2017/0216056 A1* | 8/2017 | Hill ........................ A41D 27/06 |

FOREIGN PATENT DOCUMENTS

| CN | 103889371 A | 6/2014 |
| CN | 103655011 B | 4/2016 |
| DE | 102011116280 A1 | 4/2013 |
| DE | 102014001000 A1 | 7/2014 |
| DE | 102016113590 A1 | 2/2017 |
| RU | 116343 U1 | 5/2012 |
| SU | 1739990 A1 | 8/1989 |
| WO | 2014143730 A1 | 9/2014 |
| WO | 2015153075 A1 | 10/2015 |

\* cited by examiner

PROSTHETIC SOCKET SYSTEM, AND PROSTHETIC SOCKET AND LINER

TECHNICAL FIELD

The invention relates to a prosthetic socket system with a prosthetic socket and a liner, wherein the prosthetic socket has a distal end region, at least one socket wall extending therefrom in proximal direction and connection means for securing a prosthetic component, wherein the socket wall, when in the applied state, at least partially encloses a stump that is received in the prosthetic socket, and the liner has a proximal entry opening and a lateral wall extending in distal direction, which, when in the applied state, at least partially surrounds a stump and is arranged between the stump and the prosthetic socket when in the applied state and a coupling device is arranged between the liner and the prosthetic socket in the distal end region.

BACKGROUND

Prosthetic sockets serve to secure a prosthetic component, for example an articulating device, a prosthetic foot or a prosthetic hand, to a stump of a limb. For this, the prosthetic socket provides a sufficiently dimensionally stable socket wall which at least partially encloses the stump extensively. The forces are transferred from the prosthetic component to the stump via the socket wall and a distal end region. In order to increase wearer comfort and in order to be able to secure the prosthetic socket to the stump, a liner or prosthetic liner is provided which abuts the stump. Generally, the liner consists of an elastic material and has a proximal entry opening. Frequently, silicon or another polymer which adheres to the skin surface is used as liner material. The prosthetic socket and the liner can be coupled via a distally arranged locking system, a so-called pin lock or via a negative pressure system.

A magnetic coupling device with a socket and a liner is known from U.S. Pat. No. 8,999,004 B2. A permanent magnet is arranged within the shaft. An assembly plate is arranged at the liner, which plate, depending on orientation, is pulled into the prosthetic socket or is pushed out therefrom by the permanent magnets.

SUMMARY

The object of the present invention is to provide a prosthetic socket system, a prosthetic socket and a liner, with which an improved wearer comfort and simplified insertion into the prosthetic socket are possible.

According to the invention, this object is achieved by a prosthetic socket system and by a prosthetic socket and a liner. Advantageous embodiments and developments in the invention are disclosed in the description and the Figures.

The prosthetic socket system according to the invention with a prosthetic socket and a liner, wherein the prosthetic socket has a distal end region, at least one socket wall extending therefrom in proximal direction and connection means for securing a prosthetic component, wherein the socket wall, when in the applied state, at least partially encloses a stump that is received in the prosthetic socket, and the liner has a proximal entry opening and a lateral wall extending in distal direction, which, when in the applied state, at least partially surrounds a stump and is arranged between the stump and the prosthetic socket when in the applied state, wherein a coupling device is arranged between the liner and the prosthetic socket in the distal end region, provides that on the outer side of the lateral wall of the liner and on the inner side of the socket wall resistance regions are arranged or formed which interact with one another, which regions counteract a movement extracting the liner out of the prosthetic socket, in proximal direction. A form-locking or friction-locking coupling of the distal end region of the prosthetic socket with the liner, preferably with a distal end cap of the liner, is provided by the coupling device in the distal end region of the prosthetic socket, with which the liner is prevented from coming loose from the prosthetic socket during the swing phase or during a tensile load of the prosthetic socket by the stump. A loss in contact in the distal region is prevented by the coupling device. Such a coupling between the liner and the prosthetic socket is advantageous in particular in prosthetics of the bottom extremity, as comparably large masses and large accelerations occur there, with the result that large tensile forces are exerted on the prosthetic socket system for example during the swing phase. On the outer circumference of the liner and correspondingly at the inner circumference of the socket wall, in each case at least one resistance region is arranged or formed in addition to a distal coupling device, which region, in interaction with the corresponding resistance region, counteracts a movement extracting the liner out of the prosthetic socket. In addition to the holding force, a transfer of power is provided from the prosthetic socket to the stump via the liner, distributed extensively by the coupling device over the lateral wall and the socket wall over the circumferential surface, with the result that the prosthetic socket can be secured effectively to the limb.

After attaching the prosthetic socket to the stump, in order then to be able to remove this again, the prosthetic socket is preferably designed capable of being extended, whereby it is possible to enlarge the circumference of the socket, to undo the interaction of the resistance regions and thereby facilitate removal thereof from the prosthetic socket.

A development of the invention provides that the prosthetic socket has several socket wall components which can be swiveled or folded towards one another, which components are for example arranged at a support or a dimensionally stable end structure. The end structure can be formed as a dish or a cap, and have foldable securing elements for the socket wall components. At least one socket wall component can be arranged foldable at the support or the end structure, for example via a hinge joint, in order thus to make possible an enlargement of the circumference. As a result, the resistance regions are disengaged from one another or the interaction of the resistance regions is undone, with the result that after opening the prosthetic socket, only the magnetic coupling still needs to be undone in order to remove the liner from the prosthetic socket.

A development of the invention provides that the coupling device is formed as a magnetic coupling at the distal end region or end region. A purely friction-locking coupling of the distal end region of the prosthetic socket with the liner, preferably with a distal end cap of the liner, is provided by the magnetic coupling in the distal end region of the prosthetic socket. The magnetic coupling prevents a disagreeable loss in contact in the distal region. The liner can be secured to the prosthetic socket simply, in friction-locking manner and extensively via the magnet(s). No mechanical locking devices need be activated or deactivated. The alignment of the liner relative to the prosthetic socket is forgiving, meaning that additionally, the insertion movement or push-in movement into the prosthetic socket is supported. The coupling device can also be formed as a mechanical lock, for example as a pin lock or as a hook and loop fastener or another, form-locking closure, in which elements which catch with one another are secured. Locking via hook and loop fasteners or similar systems has the advantage vis-à-vis an individual locking element that the allocation upon insertion need not take place as precisely, while protection against rotation is also provided.

At least one clamping device can be arranged at the prosthetic socket, which device causes the circumference of the socket wall to be reduced. For example, socket wall components can be shifted with respect to one another via the clamping device, resulting on the one hand in adaptation to different stump volumes and on the other hand the resistance regions being able to be brought into interaction or engagement with one another. The clamping device can be formed as a belt system or cable system with a winding or unwinding device, in order, for example by rotating the clamping device, to increase or lengthen the effective length of the belt or cable. As a result, for example socket wall components are moved towards one another or shifted away from one another. In addition to the embodiment with several socket wall components, an embodiment of the invention provides that the socket wall has an open cross-section at one point, and the opposing edges overlap one another, with the result that the circumference of the prosthetic socket is reduced or increased by activating the clamping device.

The prosthetic socket can be pretensioned elastically in or counter to a radial extension movement, with the result that the circumference of the prosthetic socket has to be reduced via the clamping device. As a result, it is easier to open the prosthetic socket. Alternatively, a pretensioning force in the direction of a reduction in the circumference can be produced, with the result that the prosthetic socket must be opened with a pretensioning force for entry, with the result that the prosthetic socket attaches itself to the liner automatically after loosening.

The prosthetic socket may be formed to be self-closing, for example by a belt system, which is arranged at a foldable socket wall component and causes the components to swivel against one another when inserting the liner into the prosthetic socket. A tensioning or closing force acting in circumferential direction can also be applied by a corresponding belt guide to the socket wall upon insertion into the prosthetic socket.

The prosthetic socket can be formed modular with a support and socket wall components secured thereto and produced separately. The socket wall components can be fixed, reversibly or irreversibly, to the support. It is possible via the modular design to use industrially prefabricated parts and to design these to be adjustable in particular in respect of the length of the prosthetic socket. It is possible to achieve a simple adaptation of the overall length of the socket by shortening the components.

Magnets with alternating polarity can be arranged in the distal end region and/or in a distal liner end region, in order to provide an alignment and orientation of the prosthetic socket relative to the liner, also in circumferential direction. A fixed allocation of the prosthetic socket to the liner results due to the corresponding polarity, with the result that an additional anti-rotation device can be dispensed with.

The resistance regions can be formed or equipped with form-locking elements and/or adhesion regions. The form-locking elements can be formed as skin, stretched velvet or also hook and loop fasteners. The resistance regions can be formed with naps, grooves, juts, undercuts, coupling regions, roughenings or other shapes. Additionally, or alternatively, resistance regions can be formed as adhesion regions which cause an adhesion of the liner to the prosthetic socket. By folding and/or extending the circumference it is possible to bring the respective resistance regions out of interaction or out of engagement with one another, with the result that extraction from the prosthetic socket is also possible.

Permanent magnets or at least one ferromagnetic element can be arranged in the distal end region. The respectively corresponding component is then arranged in the liner end region to form a magnetic coupling with the prosthetic socket, thus at least one ferromagnetic element is arranged with a permanent magnet or a permanent magnet if a ferromagnetic element is arranged in the end region. In the arrangement of permanent magnets both in the end region and also in the liner end region, attention is to be paid to a corresponding pole orientation in order to provide a secure magnetic coupling.

A metal plate with a fixing device, for example a screw thread, can be arranged to secure the distal connection means in the distal end region of the prosthetic socket. The connection means are in particular a pyramid adapter or a receiver for the pyramid adapter.

A development of the invention provides that the resistance regions are formed switchable and/or a separating device can be positioned, in particular can be pushed in, between the prosthetic socket and the prosthetic liner, with the result that a separating layer or a separating element can be brought at least partially between the resistance regions. The resistance regions or at least one resistance region can have elements which are inclined in insertion direction into the prosthetic socket or can be brought out of a locked position into a released position or vice versa. For this, the elements can be shifted into another orientation or into an exposed and withdrawn position. It is thereby achieved that the resisting force against the extraction movement is reduced and pulling out or extraction from the prosthetic socket is simplified. The shifting or reorientation of the elements into the resistance regions can take place mechanically or in a different manner, for example via switchable magnets. The separating device is for example formed as a slider which is secured capable of being shifted at the prosthetic socket, or is formed as a separate component. The separating device can be displaceably or rotatably housed at the prosthetic socket, for example in a pocket or a receiving space which is arranged next to the resistance region. If a separation of the resistance regions is intended to take place, the separating device is pushed between the resistance regions with the result that only the magnetic forces need be overcome in order to effect withdrawal from the prosthetic socket. The design of the prosthetic socket system with a prosthetic socket and a prosthetic liner with interacting resistance regions and a separating device can also be used independently of an additional magnetic coupling, and is formed as a separate solution.

The resistance regions can have retaining elements or resistance elements which are housed articulated or flexible, which elements form a progressive friction system with the outer side of the prosthetic liner because of their alignment or position. For extraction from the prosthetic socket, these retaining elements or resistance elements, which for example can be formed as stays, bristles, scales, pins or projections, can be unlocked and disengaged, or brought out of contact or interaction with the liner.

The retaining elements or resistance elements can penetrate through the separating device or penetrate into the resistance position via the separating device. For example, recesses can be present in the separating device through which retaining elements or resistance elements project. To reduce or remove the resistance or to separate the resistance regions from one another, the separating device is shifted into an unlocked position, for example by rotation or displacement. Thereby, the retaining elements or resistance elements are bent back from the surface of the liner, a blocking layer is placed between liner and prosthetic socket or causes another uncoupling, whereby the liner can be pulled out from the prosthetic socket. The separating device can also be formed as film. It is possible, via a corresponding separating device, to remove this from a closed-walled socket without problems, without applying greater forces.

The embodiments in respect of the claimed prosthetic socket system apply mutatis mutandis also to prosthetic socket systems without additional coupling devices in the distal end region.

The prosthetic socket for use in a prosthetic socket system described above has a distal end region, at least one socket wall extending therefrom in proximal direction and connection means for securing a prosthetic component, wherein the socket wall, when in the applied state, at least partially encloses a stump that is received in the prosthetic socket, and a magnetic coupling is arranged in the distal end region, and provides that on the inner side of the socket wall, at least one resistance region is arranged or formed which counteracts a movement extracting a liner out of the prosthetic socket, in proximal direction.

In a development of the invention, it is provided that the prosthetic socket can be extended radially, with the result that storing the prosthetic socket is made easier. The coupling between the resistance regions is undone or at least significantly reduced, with the result that an extraction movement is made easier by shifting the prosthetic socket from the liner.

The prosthetic socket can have several socket wall components which are swivelable to one another or foldable, wherein at least one clamping device can be arranged at the prosthetic socket which causes a reduction in the circumference of the socket wall. The prosthetic socket can be pretensioned elastically in or counter to a radial extension movement and optionally be formed with a belt system, whereby the prosthetic socket is formed to be self-closing. In a pretensioning counter to an extension movement, the prosthetic socket is formed to be self-closing via the elastic pretensioning.

The prosthetic socket is preferably formed modular and has a support and socket wall components secured thereto and produced separately, in order to be able to tailor individually prefabricated components easily. The socket wall components can be arranged reversibly at the support or at securing elements arranged or secured thereto, in order to make possible an adaptation to changing conditions in the patient.

In particular permanent magnets with alternating polarization, or a ferromagnetic element, can be arranged in the distal end region of the prosthetic socket and/or in the liner end region magnets. The ferromagnetic element can serve simultaneously as abutment for securing the distal connection means and have a securing device, e.g. a screw thread, for fixation thereof.

The resistance region on the inner side of the lateral wall can be formed with form-locking elements and/or adhesion regions and/or suction cups or a suction cup region, in order to make possible a form-locking or friction-locking coupling to the outer side of a liner. The resistance regions can have magnets or even hook and eye fasteners. The resistance region is preferably formed switchable or has switchable resistance elements, with the result that it is possible to set when and to what degree there is resistance to an extraction movement or an extraction movement is blocked or released.

A liner for use in a prosthetic socket system, as described above, provides a proximal entry opening and a lateral wall extending in distal direction, which, when in the applied state, at least partially surrounds a stump and, when in the applied state, is arranged between the stump and a prosthetic socket, wherein a magnetic coupling is arranged in a distal end region, wherein, on the outer side of the lateral wall of the liner, at least one resistance region is arranged and formed which counteracts a movement extracting the liner out of the prosthetic socket, in proximal direction.

The resistance region(s) can be formed or equipped with form-locking elements and/or adhesion regions. Magnets, in particular with alternating polarity or at least one ferromagnetic element, can be arranged in the distal liner end region, in order to cause a magnetic coupling with a prosthetic socket. The magnets are preferably formed as permanent magnets.

BRIEF DESCRIPTION OF THE DRAWINGS

Exemplary embodiments of the invention are explained in more detail below with the help of the attached Figures, in which.

DETAILED DESCRIPTION

Figure 1:
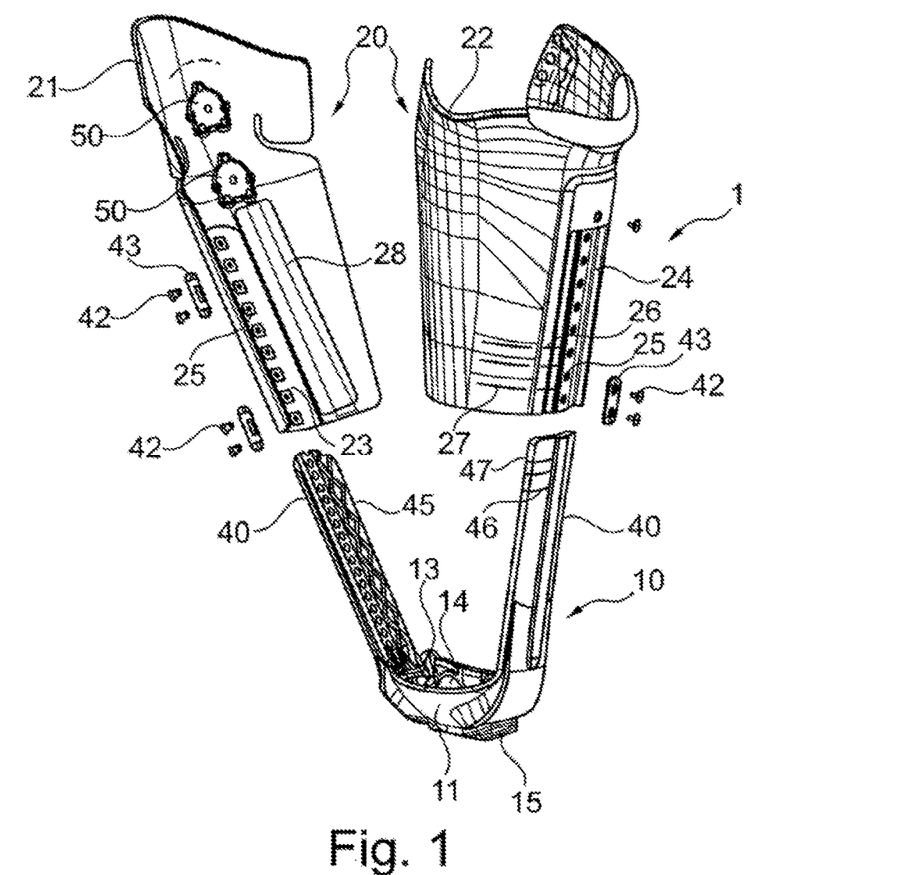
FIG. 1—shows the explosion diagram of a prosthetic socket.

FIG. 1 shows, in an explosion diagram, a prosthetic socket 1 with a support 10, to which two socket wall components 21, 22 are detachably secured. In assembled and attached state, the two socket wall components 21, 22 completely surround the stump which is not shown and form a socket wall 20 which encloses the stump. In an alternative embodiment, the socket wall 20 can also be formed as one piece, and have either a closed cross-section or an open cross-section.

Support 10 in the shown embodiment example has, at its distal end, a dimensionally stable cap 11, onto the distal side of which connection means, not shown, can be secured for a further prosthetic component, for example a prosthetic knee joint. This dimensionally stable cap 11 serves as a support for the end of the stump which is not shown, and has at least one holding device 14 for fixing or securing the stump, or a liner attached to the stump, to the prosthetic socket 1. This holding device 14 is formed as a hook and eye fastening component in the shown embodiment example, but in an alternative embodiment, other form-locking devices or even a magnetic securing can be built in, in order via corresponding form-locking elements or ferromagnetic components to cause a securing of the distal end of the liner to the support 10 and thus to the prosthetic socket.

Figure 2:
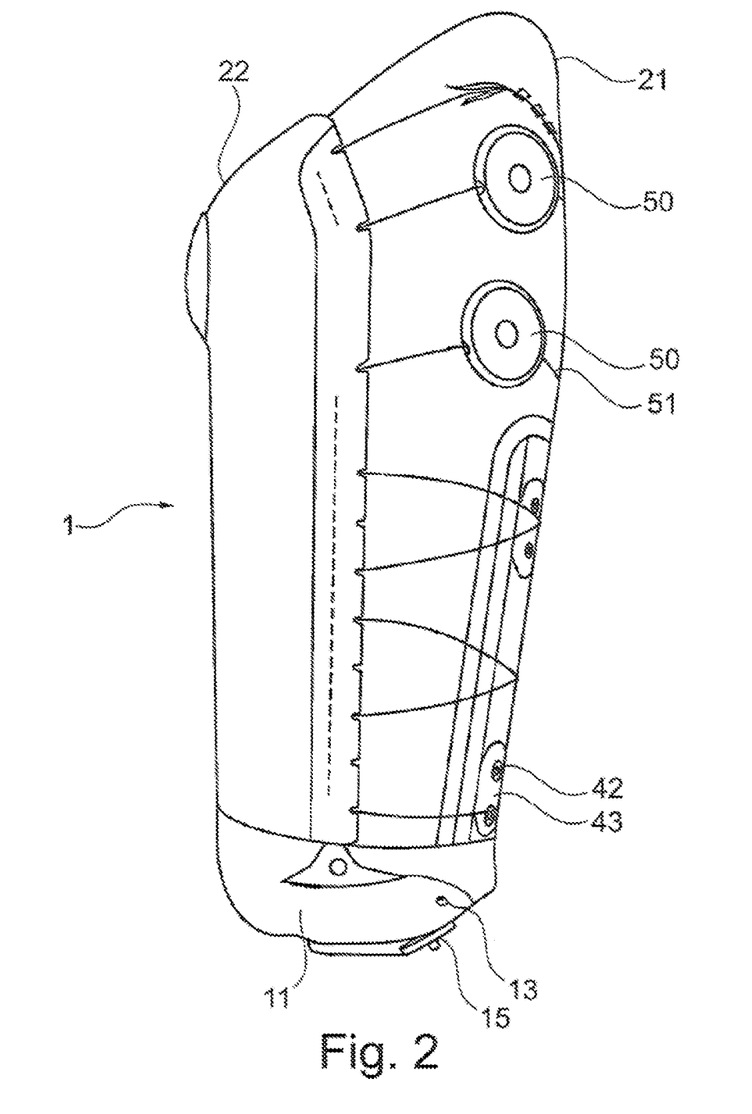
FIG. 2—shows a prosthetic socket in the assembled state.
Figure 3:
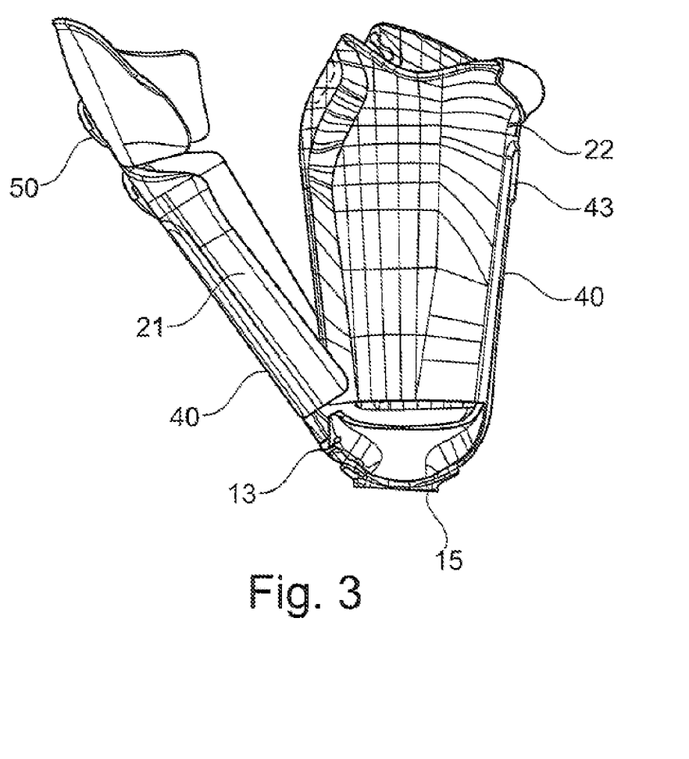
FIG. 3—shows a side view of an assembled prosthetic socket.

FIGS. 1-3 show a connection element used to connect the prosthetic socket system to a prosthetic component. The connection element, also referred to as a connection means, may be, in particular, a pyramid adapter or a receiver for a pyramid adapter.

Two securing elements 40, which are formed as rails, are extended in proximal direction from the dimensionally stable cap 10. The securing elements 40 are positioned in the applied state of the prosthetic socket 1 on the medial and lateral side of the stump and can have either the same length or different lengths, wherein preferably a greater length is provided on the lateral side. Through bores 45 are arranged as form-locking elements within the securing elements 40 formed as rails for securing socket wall components 21, 22. The through bores 45 can be provided with a screw thread and are arranged at a defined distance from one another, one behind the other, in longitudinal extension of the securing elements 40. Securing element 40 arranged laterally is arranged foldable to the support 10 via a hinge 13, the medial securing element 40 is formed in one piece on the distal cap 11, with the result that an L-shaped, rigid base is formed. In addition to a swiveable housing of the medial securing element 40, this can also be arranged displaceable on the support 10, in order to make possible an adaptability of the stump width in the distal region. In principle, it is also possible to develop both securing elements 40 to be foldable or also arrange or thus form the medial securing element 40 rigid on the dimensionally stable cap 11. Also, more than two securing elements 40 can be formed on the support or can be arranged there.

The socket wall components 21, 22 and thus the overall socket wall 20 can be secured detachably on the support 10. For this, guides 23, 24 for the securing elements 40 are secured to the outer sides of the socket wall components 21, 22. The guides 23, 24 are formed as rail receivers which are formed corresponding to the rail-type design of the securing elements 40 and can receive these within themselves. The guides 23, 24 can be formed C-shaped, wherein the cross-section of guides 23, 24 permits either a lateral introduction of securing elements or has roof limbs aligned towards one another, with the result that the respective securing elements 40 can be pushed into the corresponding guide 23, 24 only in longitudinal extension. The lateral walls of the guide 23, 24 can also be formed inclined to one another, with the result that the securing elements 40 are guided fixed both in medial direction and also in lateral direction, but also are guided displaceable in guides 23, 24 in longitudinal extension of the securing elements 40.

Corresponding to the through bores 45 in the securing elements 40 bores with internal threads 25 are arranged in the guides 23, 24, which bores are arranged spaced apart from one another in longitudinal extension behind one another, in which they are flush to the through bores 45. The socket wall components 21, 22 are connected to the respective securing element 40 via form-locking elements 42 in the form of screws. For this, the securing elements 40 are introduced into the guides 23, 24 until the desired length is achieved. The through bores 45 and the internal thread within the guides 23, 24 are aligned towards one another and the screws 42 are inserted and fixed. A form-locking, detachable securing of the socket wall 20 to the support 10 is thereby achieved. Through bores 45 can also be formed as oblong holes in order to make possible a quasi-continuous adjustment of the position of the socket wall components 21, 22 relative to the support 10. An oblong hole, extending over the whole length, can also be formed with the result that, in addition to a form-locking fixing of the socket wall 20 to the securing elements 40, the longitudinal displaceability along the guides 23, 24 is blocked, clamping via the screws 42 and a plain washer 43.

In the distal region of the socket wall components 21, 22, markings 26 and material weakenings 27 transverse to the longitudinal extension are attached aligned, in order to shorten the overall length if necessary. The material weakenings 27 can extend over the whole circumference of the socket wall component 21, 22, in the case of a one-piece design of the socket wall 20, over its full extent. Markings 26 are preferably oriented at uniform distances from one another and can be provided with a scale in order to make it easier to adapt the length. Corresponding markings 46 and material weakenings 47 are arranged at the securing elements 40, preferably at the proximal ends thereof, and make possible an individual adaptability of the length of the whole prosthetic socket 1.

The socket wall components 20, 21 form a proximal socket portion as socket wall 20, the support 10 with the securing elements 40 forms a distal socket proportion, which are formed and arranged longitudinally displaceable to one another and securable to one another, with the result that they are continuous or can be step-adjusted and fixed. By shortening the distal socket proportion in the design of the support 10 and/or of the proximal socket proportion in the design of the socket wall 20, a reduction in the socket length can be achieved, whereby it is possible to introduce industrially prefabricated socket parts, in order to be able to adapt a prefabricated socket to individual stump lengths. The desired load can also be adapted and adjusted to the stump end.

A clamping device 50 is arranged at the lateral socket wall component 21, via which device the socket width can for example be varied via a cord-cable-belt system. On the basis of the two-part design of the socket wall 20 in the embodiment example shown and the foldable storage of the lateral socket wall component 21 to the support 10, it is possible and necessary to fix the position of the socket wall components 21, 22 to one another in circumferential direction. It is possible, due to the foldability of the support 10 and the extendibility of the prosthetic socket 1 achievable as a result, to make it easier to insert same into the prosthetic socket. Likewise, it is possible as a result to arrange or form form-locking elements 28 at the inner side of the socket wall which impede or prevent a movement in proximal direction. Thus, at the inner side of the socket wall 20 a hook and loop fastener, a skin or a surface structuring can be arranged or formed which engages in form-locking manner in a corresponding structure on the liner. Due to the folding movement, a peeling process or disengagement can take place, with the result that a corresponding separation of prosthetic socket 1 and liner is easily possible.

In the embodiment example of FIG. 1 which is shown, the socket wall components 21, 22 are designed differently. The medial socket wall component 22 extends over more than half the overall circumference, here ¾ of the overall circumference, whereas the lateral socket wall component 21 is dimensioned such that there is a supplementation of the circumference, with the result that the prosthetic stump can be fully enclosed. The side edges of the socket wall components 21, 22 can overlap one another when in inserted state as well as assembled state, and thereby make it possible to adjust the width also in the course of wearing, if there are discrepancies in stump volume.

A finished, assembled prosthetic socket 1 is shown in FIG. 2. The distal, dimensionally stable cap 11, the hinge device 13 for the lateral securing element 40 and the socket wall 20 from a lateral socket wall component 21 and a medial socket wall component 22 can be seen. In the embodiment example shown, the clamping device 50 has two rotation mechanisms, via which the effective length of two cables 51 can be changed. The cables or ties 51 are arranged at the opposite side edges of the medial socket wall component 22, causing a reduction in the circumference due to the shortening. By rotating the clamping devices 50 in opposite direction, the circumference of the prosthetic socket can be extended. The lateral socket wall component 21 is detachably fixed to the support 10 via a total of four screws 42. Screws 42 are guided through the through bores 45 into the securing element 40 and screwed into the inner thread 25 inside the guide 23. An additional clamping effect results from the plain washer 43.

FIG. 3 shows, in a lateral view, the prosthetic socket 1 in a folded state, wherein the two socket wall components 21, 22 are already secured to the support 10. The two socket wall components 21, 22 extend as far as the dimensionally stable cap 11 in assembled state, with the result that the prosthetic socket 1 almost completely encloses the stump, not shown, with the liner. It can likewise be seen from FIG. 3 that the left-hand socket wall component 21 covers the right-hand socket wall component 22 partly at the edges, with the result that the prosthetic socket 1 fully surrounds the stump over almost the whole length.

Figure 4:
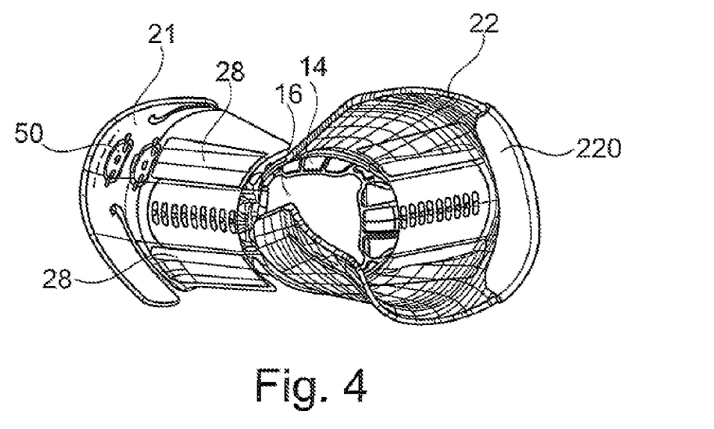
FIG. 4—shows an inclined top view according to FIG. 3.

In FIG. 4, the prosthetic socket 1 is shown in the embodiment according to FIG. 3 in a top oblique view. Clamping devices 50 can be seen on the frontal socket wall component 21, likewise the resistance regions 28 can be seen on the inner side of the frontal socket wall component 22. The second socket wall component 22 surrounds the stump, not shown, over more than three quarters of the circumference. On the basis of the open cross-section of the socket wall component 22, an extension of the prosthetic socket 2 is possible in circumferential direction. Cushioning 220 is arranged at the proximal, posterior edge region of the posterior socket wall component 22, which cushioning consists of a softer material than the conventional socket wall component 22, in order to provide padding through which wearer comfort is increased. Resistance regions 28 are likewise formed at the inner side of the second socket wall component 22, which regions interact with the prosthetic liner, not shown, and provide resistance to an extraction movement from the prosthetic socket 2 or form a form-locking lock between the liner and the prosthetic socket 1.

Figure 5:
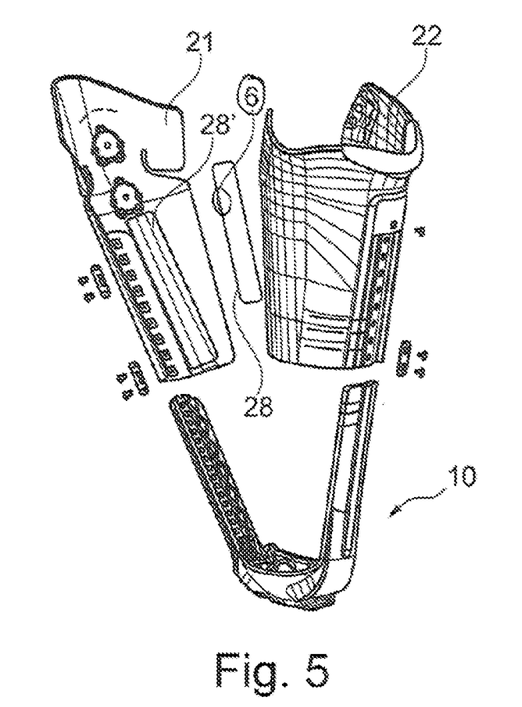
FIG. 5—shows a variant of FIG. 1.

FIG. 5 shows a variant of FIG. 1 with the prosthetic socket 1 in a not yet assembled state. Instead of the resistance regions 28 formed in the frontal socket wall component 22, which regions are for example provided by a corresponding corrugation, a saw-tooth design of the surface, by naps, grooves, or another profile, a securing region 28' is arranged at the frontal socket wall component 21 for a separately produced resistance region 28. The resistance region(s) 28 are detachably secured to the respective socket wall component 21, 22 and thus make possible an exchange due to wear or an adaptation to the respective user, for example by increased adhesion of the liner to the prosthetic socket 1.

Figure 6:
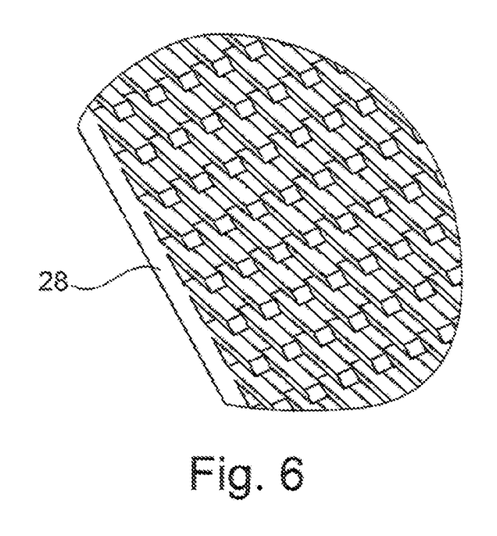
FIG. 6—shows a detailed view of a resistance region.

The surface of the resistance region 28 is shown enlarged in FIG. 6. Equidirectional stays, naps or fibers can be seen which are inclined to the distal end or the dimensionally stable cap 11, with the result that no, or only a small resistance of the introduction movement is opposite when sliding into the prosthetic socket 1. Due to the sliding-in, the naps, stays or fibers are introduced and make it possible to slide the prosthetic liner along during insertion. In an opposite direction, the tips of the stays, naps or fibers engage, and are aligned, whereby a radial pressure is exerted on the prosthetic liner and simultaneously an extraction movement is blocked on the basis of the resistances provided by the stays, naps or fibers. The stays, naps or fibers can be formed comparatively kink resistant, with the result that, when extracting or moving opposite the direction of introduction, bending is not possible, or possible only with difficulty.

For storing the prosthetic socket 1, the clamping device 50 can be opened and the one socket wall component 21 can be folded from the prosthetic liner and/or the open cross-section of the other socket wall component 22 can be bent, with the result that the liner with the stump can be removed easily from the prosthetic socket 1. Merely the magnetic forces have to be overcome by the magnetic coupling in the distal end. The magnets arranged at the prosthetic liner 2 can adhere to the metal plate 16 which is present on the inner side of the dimensionally stable cap 11.

A variant for loosening or providing the possibility of withdrawal from the prosthetic socket 1 is provided by a separating shield being introduced between the outer surface of the prosthetic liner and the inner surface of the prosthetic socket 1, for example a plastic disk which is formed flat and is nestled against the contour of the stump. Once the resistors which act in form-locking manner, such as stays, naps, structural elements or directed fibers of the resistance regions 28, are covered by the disk or the separating device, there is no further interaction between the resistance regions and the prosthetic liner can be withdrawn easily from the prosthetic socket 1 together with the stump.

Figure 7:
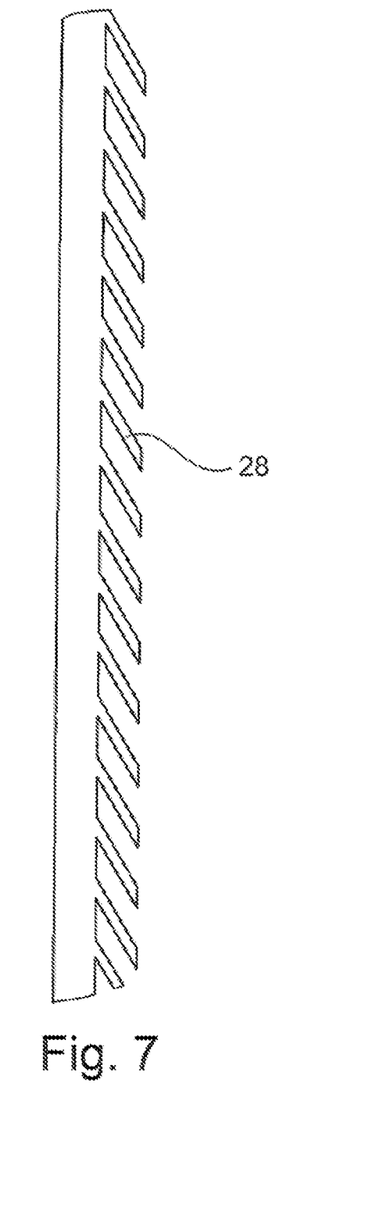
FIG. 7—shows a sectional view through a resistance region.

In FIG. 7, the orientation of the stays of the resistance regions 28 is shown in a sectional representation. It can be seen that a smooth outer wall is present on the opposite side of which the structural elements, such as stays, ribs, naps, or the like are arranged inclined in the insertion direction indicated by the direction of the arrow.

Figure 8:
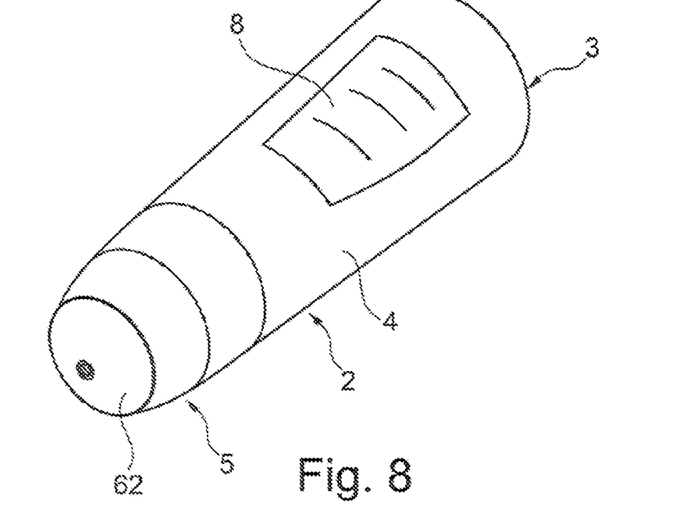
FIGS. 8 and 9—show views of prosthetic liners.

FIG. 8 shows a prosthetic liner 2 with a proximal entry opening 3 and a distal end cap in a distal liner end region 5. The distal end cap can for example be formed as a ferromagnetic plate 62 which has a thread for receiving a locking element, for example a pin, or for connection to a suction device. A closed lateral wall 4 extends in proximal direction from the distal liner end region 5, at the outer side of which wall a resistance region 8 is arranged which extends in the shown embodiment example up to just below the proximal entry opening 3. The resistance region 8 can be formed by shaping a form-locking engagement with the components of the correspondingly formed resistance regions 28 of the inside of the socket. Additionally, or alternatively, adhesion regions can be arranged or formed at the outer side of the lateral wall 4 of the prosthetic liner 2, in order to provide an increased resistance to an extraction movement of the liner 2 from the prosthetic socket 1 in proximal direction. The resistance region 8 can also be formed as a mesh, fleece, stretched velvet, as directed fibers, naps, stays, ribs, magnet region, hook and eye fastener or suction cups or the like. The material of the liner 2 is preferably elastic in the region of the lateral wall 4. Advantageously, the liner consists of an elastomer such as silicon, polyurethane or TPE. Alternatively, the liner can also consist of a spacer fabric. Advantageously, in this case, the spacer fabric is coated, on the side facing the body, at least partially with an adhesive elastomer in order to prevent a withdrawal. A spacer fabric is advantageous as this is breathable. The liner itself can be provided with a textile or friction-minimizing surface coating in order to simplify insertion. The textile can serve as a resistance region, with the result that no further resistance region is necessary. A matrix can additionally be provided in or at the liner, this preventing the so-called "milk effect" by reducing longitudinal elasticity.

Figure 9:
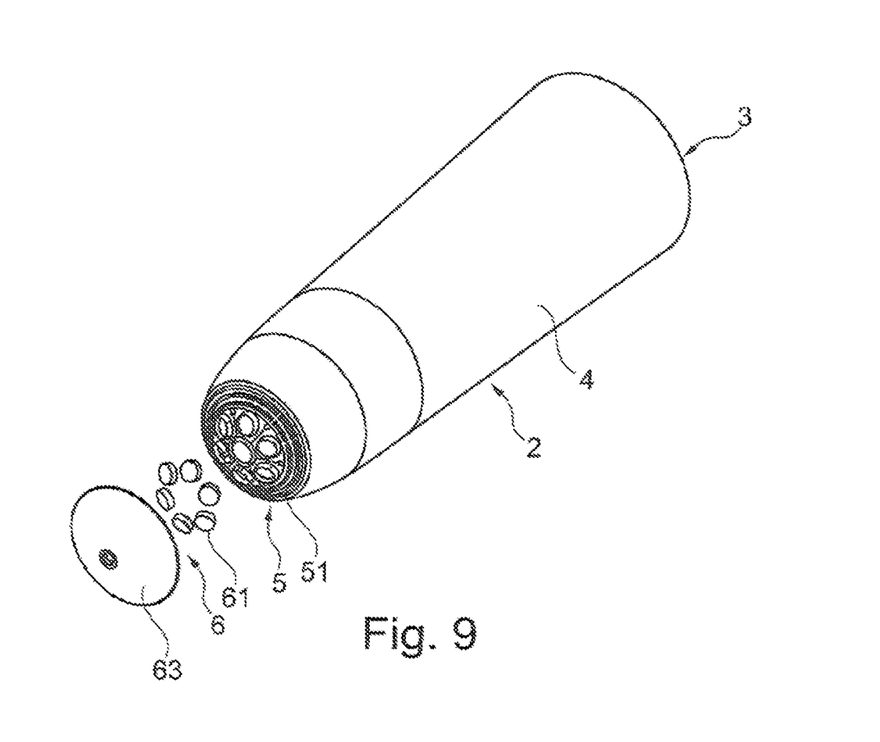

A variant of the prosthetic liner 2 is shown in FIG. 9, in which magnets 61 are arranged beneath a distal end cap 63, which magnets are arranged in recesses inside the distal liner end region 5. For this, receivers or holders for magnets 61 are provided in a liner end cap 51. Magnets 61 can have an alternating polarity, with the result that an angle orientation and alignment of the liner 2 relative to, for example, correspondingly arranged magnets are possible in the dimensionally stable cap 11. In addition to an adhesion via the magnetic closure in the liner end region 5 and the adhesion, locking or resistance by the resistance regions 8, 28, the prosthetic socket 1 is secured, rotation-resistant, relative to the liner 2 as a result. Increased safety for the user of the prosthetic socket system results from the prosthetic socket in conjunction with the prosthetic liner 2 shown.

It is possible, via a ferromagnetic element 16, 62 in conjunction with permanent magnets 14, 61 or by a direct magnetic coupling of several permanent magnets with one another, to provide a lock in the distal end region in addition to an adhesive or form-locking connection in the lateral wall region and the prosthetic socket region, which locking makes possible a precise alignment of the liner 2 with the stump within the prosthetic socket 1, without requiring highly accurate insertion of a form-locking lock, for example in the design of a pin lock.

Figure 10:
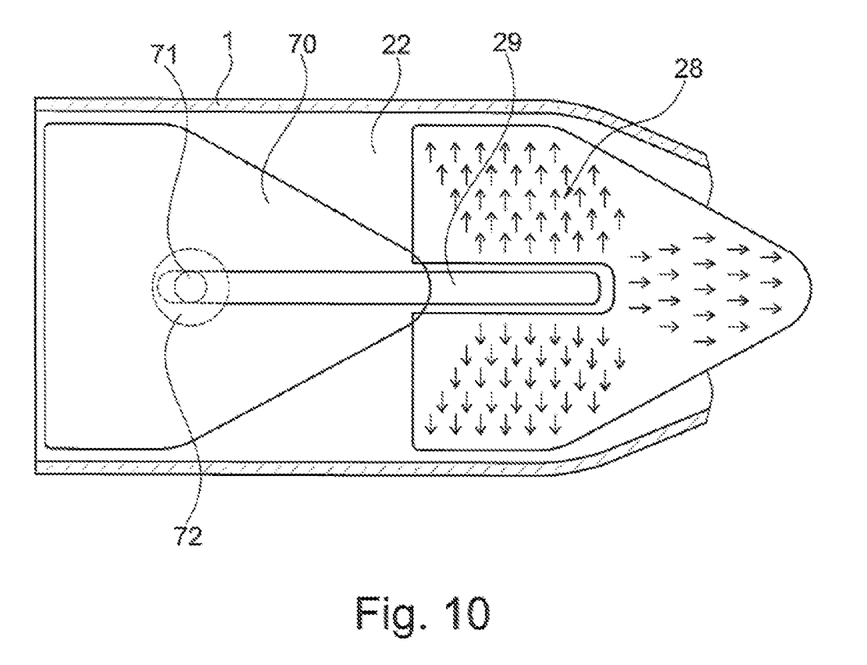
FIG. 10—shows a detailed view of a resistance region with a separating device.

FIG. 10 shows, in a schematic sectional representation, a prosthetic socket 1 with retaining elements or resistance elements arranged on the inner side, which elements are arranged in a resistance region 28. The arrows in resistance region 28 point to the different resistance directions in which a maximum resistance to a movement along the surface is provided. In addition to different resistance directions, it is also possible that a resistance is provided only against one direction, for example an insertion direction of the prosthetic socket.

Within the prosthetic socket 1, a longitudinal slit 29 is formed in the socket wall 22, in which slit a pin 71 is displaceably housed. Pin 71 has, on its outer side, an actuating element 72 or a handle via which the pin 71 can be displaced along the recess 29. The actuating element 72 is accessible from the outer side of the prosthetic socket 1, in particular it is arranged on the outer side of the socket wall 20. On the side within the prosthetic socket 1 which is abutting the socket wall 22 and opposite the actuating element 72, a separating device 70 is arranged which is formed as a disk, separating shield or film. In the embodiment example shown, the separating device 70 is formed substantially triangular, with one tip pointing in the direction of the distal end of the prosthetic socket 1 which is only illustrated.

In the state shown, the separating device 70 is located substantially disengaged from the resistance region 28 and the retaining elements, resistance elements or the like, arranged therein. To separate form-locking engagement of the resistance regions 8, 28 from one another or also to undo a friction-locking connection or to switch the resistance elements or retaining elements from an engaged position into a detached position, in which the prosthetic liner, not shown, can be moved out of the prosthetic socket 1, the separating device 70 is pushed to the right and shifted via the resistance region 28. The resistance regions 8 and 28 of the liner and the prosthetic socket are thereby disengaged, uncoupled or have their adhesive forces or resistant forces reduced, and are removed from interaction, with the result that the patient can withdraw from the prosthetic socket 1. The inner side of the separating device 70 is preferably formed with smooth walls. The separating device 70 can be formed flexible, in order to be adapted to the contour of the socket and stump.

Due to the different orientations of the resistance elements, retaining elements or resistance sections in the resistance region 28, in addition to a reduction in inclination for the extraction movement, a fixing of the prosthetic liner inside the prosthetic socket 1 is provided, in terms of a rotation about a longitudinal axis. The rotational stability of a prosthetic socket relative to a prosthetic liner is an essential factor for the feeling of stability felt by a user, and can be provided by the differently aligned orientations, for example by differently directed bristles, fibers, stays, scales, channels, surface structures or the like. The resistance elements can be elastically housed or flexibly formed.

Figure 11:
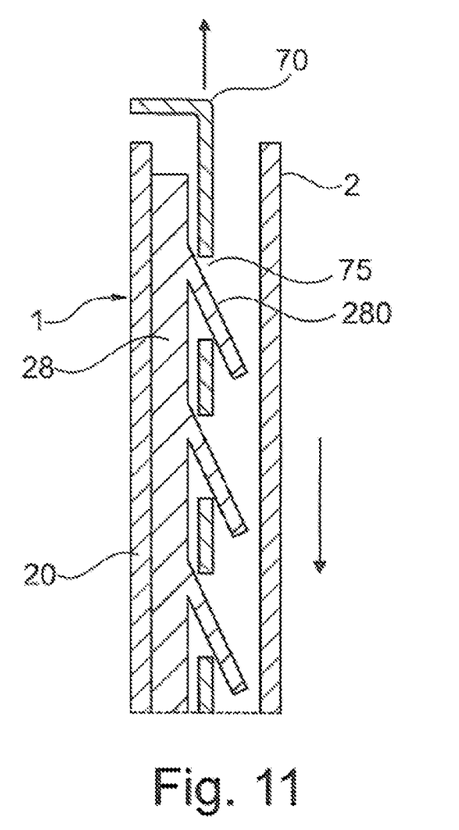
FIG. 11—shows a schematic sectional representation through an attached prosthetic socket system.

A further variant of the separating device is shown in FIG. 11, in which a schematic partial view of a prosthetic socket system with a prosthetic socket 1 and a liner 2 arranged therein is shown. A resistance region 28 is attached on the inner side of the socket wall, which region has resistance elements 280 or retaining elements pointing inwards, and which are inclined to an insertion direction which is indicated by the downwards pointing arrow. A separating device 70 is provided with recesses 75 through which the resistance elements 280, which in the shown embodiment example are formed as a plurality of stays, bristles or ribs, penetrate. In the shown position, the resistance elements 280 interact with the outer side of the prosthetic liner 2 and enable an introduction of the prosthetic liner 2 into the prosthetic socket 1, on the basis of their inclination. An opposite movement is prevented or at least impeded by the resistance elements 280 as the resistance elements 280 or retaining elements would be positioned against the outer wall of the prosthetic liner 2, would be bent upwards and thereby provide a resistance to an extraction movement, as the resistance elements 280 would be blocked. This effect can be reinforced by pulling out the separating device 70 formed as a disk, or pulling it upwards. When pulling the separating device 70 upwards, the resistance elements 280 or retaining elements are assembled and pressed against the outer wall of the prosthetic liner 2.

In order to enable or simplify the extraction movement, the separating device 70 is shifted in the insertion direction of the prosthetic liner 2. The resistance elements 280 guided through the recesses 75 thus have their inclination reinforced, and are pressed against the socket wall 20 or against the surface of the resistance region 28 and become disengaged from the prosthetic liner 2. The tips or ends of the resistance elements 280 are then located inside the recesses 75 and are projected through the inner surface of the separating device 70, with the result that there is no, or only a small, interaction between the resistance elements 280 and the prosthetic liner 2. The prosthetic liner 2 can then be pulled out of the prosthetic socket 1. In order to provide an increased resistance, the separating device 70 is shifted upwards, and the resistance elements 280 are assembled, and their inclination is changed.

The invention claimed is:
1. A prosthetic socket system, comprising:
a prosthetic socket having a distal end region, at least one socket wall extending therefrom in proximal direction and connector for securing a prosthetic component, wherein the socket wall, when in the applied state, at least partially encloses a stump that is received in the prosthetic socket;
a liner having a proximal entry opening and a lateral wall extending in a distal direction, which, when in the applied state, is configured to at least partially surround a stump and, when in the applied state, is configured to be arranged between the stump and the prosthetic socket;
a coupling device arranged between the liner and the prosthetic socket in the distal end region;
resistance regions arranged or formed on an outer side of the lateral wall of the liner and on an inner side of the socket wall, the resistance regions arranged to interact with one another to counteract a movement extracting the liner out of the prosthetic socket in a proximal direction, wherein the resistance regions interact with one another in a form-locking manner to counteract a movement extracting the liner out of the prosthetic socket in the proximal direction, and wherein the resistance regions comprise a plurality of resistance elements inclined in an insertion direction of the liner into the prosthetic socket.

2. The prosthetic socket system according to claim 1, wherein the prosthetic socket can be extended radially.

3. The prosthetic socket system according to claim 1, wherein the prosthetic socket has several socket wall components arranged swivelable or foldable to one another.

4. The prosthetic socket system according to claim 1, wherein the coupling device is formed as a magnetic coupling or a coupling device acting in a form-locking manner.

5. The prosthetic socket system according to claim 1, further comprising at least one clamping device is arranged at the prosthetic socket to cause a reduction in circumference of the socket wall.

6. The prosthetic socket system according to claim 1, wherein the prosthetic socket is pretensioned elastically in or counter to a radial extension movement.

7. The prosthetic socket system according to claim 1, wherein the prosthetic socket is formed to be self-closing.

8. The prosthetic socket system according to claim 1, wherein the prosthetic socket is formed modularly with a support and socket wall components secured thereto and separately produced.

9. The prosthetic socket system according to claim 1, further comprising magnets with alternating polarity arranged in at least one of the distal end region and a distal liner end region.

10. The prosthetic socket system according to claim 9, wherein, in the distal end region, permanent magnets or at least one ferromagnetic element, and in a liner end region a corresponding component is arranged to form a magnetic coupling with the prosthetic socket.

11. The prosthetic socket system according to claim 1, wherein the resistance regions are formed with at least one form-locking coupling.

12. The prosthetic socket system according to claim 1, wherein, in the distal end region, a metal plate is arranged with a securing device for securing the connector.

13. The prosthetic socket system according to claim 1, wherein at least one of switchable resistance regions and a separating device are positioned between the resistance regions.

14. The prosthetic socket system according to claim 13, wherein the separating device is formed as a shield which can be inserted between the prosthetic socket and the prosthetic liner.

15. The liner according to claim 1, wherein the resistance regions comprise equidirectional, kink-resistant naps, stays or fibers.

16. A prosthetic socket for use in a prosthetic socket system, the prosthetic socket comprising:
a distal end region;
at least one socket wall extending therefrom in a proximal direction, the socket wall, when in an applied state, is configured to at least partially enclose a stump that is received in the prosthetic socket;
a connector for securing a prosthetic component;
a coupling device arranged in the distal end region;
at least one resistance region arranged or formed on an inner side of the socket wall, the at least one resistance region counteracts a movement extracting a liner out of the prosthetic socket in a proximal direction, wherein the at least one resistance region interacts in a form-locking manner to counteract a movement extracting the liner out of the prosthetic socket in the proximal direction, and wherein the at least one resistance region comprises a plurality of resistance elements inclined in an insertion direction of the liner into the prosthetic socket.

17. The prosthetic socket according to claim 16, wherein the prosthetic socket can be extended radially.

18. The prosthetic socket according to claim 16, further comprising several socket wall components arranged swivelable or foldable to one another.

19. The prosthetic socket according to claim 16, further comprising at least one clamping device arranged to cause a reduction in circumference of the socket wall.

20. The prosthetic socket according to claim 16, wherein the prosthetic socket is pretensioned elastically in or counter to a radial extension movement.

21. The prosthetic socket according to claim 16, wherein the prosthetic socket is formed to be self-closing.

22. The prosthetic socket according to claim 16, wherein the prosthetic socket is formed modularly with a support and socket wall components secured thereto and produced separately.

23. The prosthetic socket according to claim 16, wherein, in the distal end region, magnets or a ferromagnetic element are arranged as a coupling device.

24. The prosthetic socket according to claim 16, wherein the resistance region is formed with at least one form-locking coupling.

25. The prosthetic socket according to claim 16, wherein the resistance region is formed switchable or has switchable resistance elements.

26. The prosthetic socket according to claim 16, wherein a separating device is arranged at the prosthetic socket.

27. A liner for use in a prosthetic socket system, the liner comprising:
a proximal entry opening;
a lateral wall extending in a distal direction, which, when in the applied state, is configured to at least partially surround a stump and, when in the applied state, is configured to be arranged between the stump and a prosthetic socket;
a coupling device arranged in a distal end region;
wherein, on an outer side of the lateral wall of the liner, at least one resistance region is arranged or formed, which counteracts a movement extracting the liner out of the prosthetic socket in a proximal direction, wherein the at least one resistance region interacts in a form-locking manner to counteract a movement extracting the liner out of the prosthetic socket in the proximal direction, and wherein at least one the resistance region comprises a plurality of resistance elements inclined in an insertion direction of the liner into the prosthetic socket.

28. The liner according to claim 27, wherein the resistance region is formed with at least one form-locking coupling.

29. The liner according to claim 27, wherein, in the distal liner end region, magnets or at least one ferromagnetic element are arranged as a coupling device.

* * * * *